United States Patent [19]

Bryant et al.

[11] 4,444,204
[45] Apr. 24, 1984

[54] SCOLIOSIS INCLINOMETER

[75] Inventors: John T. Bryant; Michael Ashworth, both of Kingston; Gerald Saunders, Bath, all of Canada

[73] Assignee: Queen's University at Kingston, Kingston, Canada

[21] Appl. No.: 372,475

[22] Filed: Apr. 28, 1982

[30] Foreign Application Priority Data

May 8, 1981 [CA] Canada .................................. 377165

[51] Int. Cl.$^3$ .............................................. A61B 5/10
[52] U.S. Cl. .................. 128/781; 33/174 D; 33/175
[58] Field of Search .............. 128/781; 33/174 D, 175

[56] References Cited

U.S. PATENT DOCUMENTS

| | | | |
|---|---|---|---|
| 1,856,779 | 5/1932 | Montelius | 33/174 D X |
| 2,162,916 | 6/1939 | Hyland | 33/175 X |
| 2,475,706 | 7/1949 | Jamieson | 33/174 D |
| 2,930,133 | 3/1960 | Thompson | 33/174 D |
| 3,047,957 | 8/1962 | Conway | 33/174 D |
| 3,955,285 | 5/1976 | Moeckl | 33/174 D |
| 4,033,329 | 7/1977 | Gregory | 33/174 D |
| 4,135,498 | 1/1979 | McGee | 128/774 |

FOREIGN PATENT DOCUMENTS 907977 of 1946 France .................................. 128/781

Primary Examiner—Lee S. Cohen
Assistant Examiner—John C. Hanley
Attorney, Agent, or Firm—Richard J. Hicks; Stanley E. Johnson

[57] ABSTRACT

A device for measuring rib hump angle in the diagnosis of scoliosis, which comprises a frame, a plurality of stiff, laterally spaced parallel finger-like members arranged in pairs along one side of the frame with the two members of each pair equally spaced on opposite sides of the centerline of the edge, and frictionally slidable on the frame parallel to the centerline of the edge, so that when the frame edge is transverse and perpendicular to the longitudinal axis of the spine each finger-like member can be pushed into contact with the back. Means are also provided on the frame to measure the angle subtended between a first line perpendicular to the movement of the fingers and a second line intersecting the first line and passing through a selected point on the highest finger on the "high" side of the spine and the corresponding point on the other finger of the pair on the other or "low" side of the spine, so that rib hump angle can be measured directly.

6 Claims, 3 Drawing Figures

U.S. Patent
Apr. 24, 1984
4,444,204
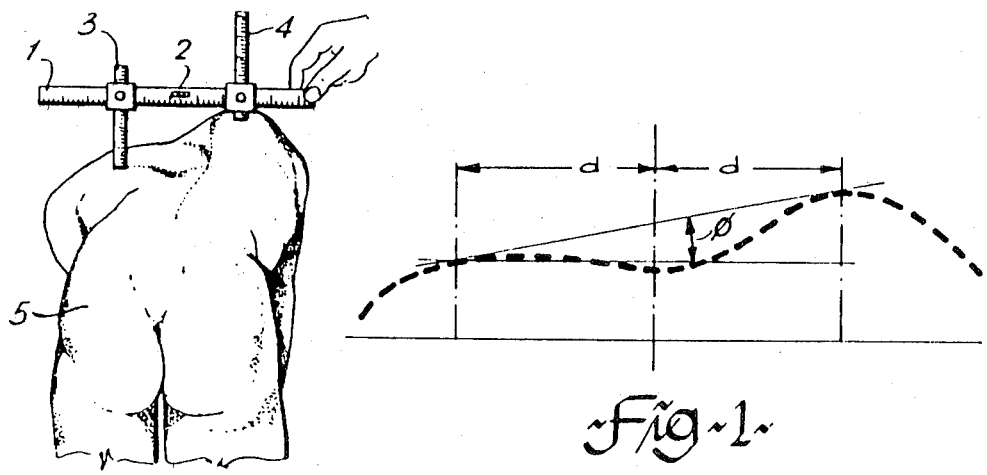
Fig-1-
Fig-2-
(PRIOR ART)
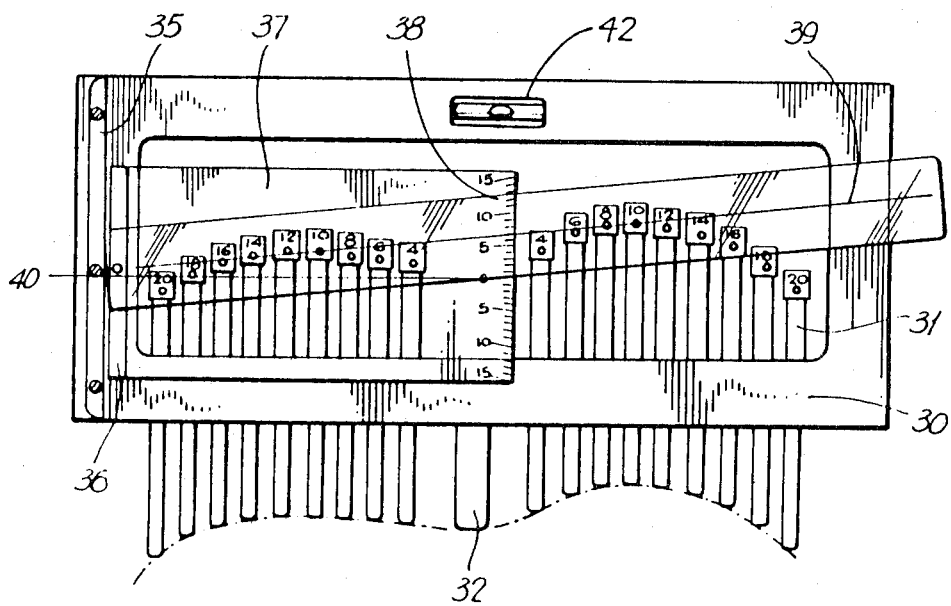
Fig-3-

SCOLIOSIS INCLINOMETER

This application relates to a device for preliminary evaluation of scoliosis, and more particularly to a device for measuring rib hump angle of the human spine.

Scoliosis or abnormal curvature of the spine is a relatively common hereditary condition among adolescents which can usually be corrected without resort to surgical methods if detected in its early stages. One of the first indications of scoliosis is the presence of a rib hump which gives the contour of the spine an assymetrical appearance, when viewed from the back, because one side of the rib cage is displaced backwards relative to the other thereby causing a rotation of the spine. Annual screening of school children to detect the presence of a significant rib hump is, therefore, highly desirable if it can be achieved at relatively low cost.

Several screening methods have heretofore been suggested. The standard clinical test, wherein the patient bends from the waist with the arms hanging freely and a physician or nurse positioned behind the patient makes a mental judgement of the rib hump as the patient turns the trunk from side to side, lacks objectivity. Rib hump angles of 3°-4°, which may be sufficient to indicate scoliosis, are difficult to assess visually and furthermore documentation of changes with time is difficult with this subjective assessment.

Moiré topography in which contour lines of an object are produced as interference fringes while the object is illuminated by a spotlight through a special screen, and the fringe pattern so produced, by the interference of the screen and its shadow on the object, affords an objective assessment method. Clinically, the patient is asked to stand erect with feet together, then photographed graphed using an apparatus constructed to accommodate patients. After developing the film, it is assessed either by viewing directly under a microscope or by using a computer system designed for the purpose. Rib hump angle is computed from the relative contour heights of the highest points on either side of the back. While the Moiré photograph is a useful clinical tool it is too prohibitively expensive for routine screening. Also, the equipment to perform the measurements is costly to purchase and maintain and specialized personnel and computing facilities are required.

Mechanical topography using a contour gauge consisting of a rule provided with a spirit level and at least one pair of downwardly depending position lockable fingers or rods, does provide a useful objective test which is preferable to the clinical test and far less expensive to perform than Moiré topography. In clinical use, the patient places hands together and flexes hips and spine until the hands are between the knees. The instrument is placed across the back and centered on the bony part of the spine. After ensuring, by means of the spirit level, that the instrument is horizontal and that each finger is in contact with the skin, all fingers are locked. The rib hump angle is calculated by measuring the height of the finger corresponding to the highest point on the hump side. The height of the finger equidistant from the mid-point on the other side is also measured. The difference is determined mentally and either by chart or table, the rib hump angle is found using the difference in height and the spacing between the fingers at which the heights were measured. The complexity of computing the rib hump angle once the back contour is known, is however, a drawback. The use of two measurements and table/graph consultation is inconvenient and prone to error.

It is an object of the present invention to provide a simplified objective test for scoliosis wherein a mechanical topography device or inclinometer provides a direct reading of the measured hump angle.

Thus by one aspect of this invention there is provided a device for use in the preliminary evaluation of scoliosis, comprising:

a frame;

a plurality of stiff, parallel, laterally spaced elongate members arranged in pairs along a side edge of the frame with the two members of one pair being equally spaced on opposite sides of a centerline of the side edge, said elongate members being longitudinally frictionally slidable on the frame parallel to the centerline of the side edge thereof; and means on said frame to determine an angle defined as a rib hump angle and subtended between a first line perpendicular to the movement of the elongate members and a second line intersecting said first line and passing through a selected position on each respective member of a selected said pair of members.

The invention will be described in more detail hereinafter with reference to the accompanying drawings in which:

FIG. 1 is agraph illustrating the definition of hump angle 1;

FIG. 2 is an elevational view of a mechanical topography device according to the prior art; and FIG. 3 is a plan view of a device according to one embodiment of the present invention.

As discussed hereinabove, and illustrated in more detail in FIG. 1, one of the first indications of scoliosis is the presence of a significant rib hump which has heretofore been measured using a device such as that illustrated in FIG. 2. Rib hump angle may be defined as that angle subtended between a horizontal reference line and a line passing through the highest point on the hump side of the back and a point equidistant from the centerline of the spine on the non-hump side. Even subtle or small rib hump angles of the order of 3°-4° may indicate that scoliosis exists and that the patient should be referred for more tests.

In FIG. 2 there is shown a device of the prior art. A calibrated rule 1 is provided with a spirit level 2 at the center thereof and a pair of movable calibrated fingers 3, 4 lockable at any position along the rule 1. The rule 1 is positioned horizontally across the back 5 of a patient with the spirit level on the centerline of the spine. Finger 4 is moved along the rule and locked into a position corresponding to the highest point of the hump. The height of finger 4 is noted as is the distance of the finger from the centerline. Finger 3 is then moved to a position equidistant from the centerline and lowered to contact the skin. The height of finger 3 is then measured and the difference in the two heights is calculated. From these measurements the hump angle $\phi$ can be calculated by reference to standard tables or charts or by first principles of trigonometry.

The device of the present invention, as illustrated in FIG. 3, can be used in a similar way to make similar measurements but in a simplified and improved manner. In the device illustrated in FIG. 3, there is provided a frame 30 through which project a plurality of parallel frictionally slidable stiff elongate members 31, such as rods or wires. A fixed locating member 32 is generally provided in the centerline of the frame and an equal number of members 31 are provided on each side of member 32. A spirit level 42 may also be provided. The members 31 are arranged in pairs with one member of each pair being equidistantly spaced on one side or the other of the central member 32 and an identifying mark, such as a number, and preferably a locator point is provided for each pair for rapid identification of a selected equidistantly spaced pair, and measurement of a selected height. Instead of a locator point the top of the member 31 or other selected point may equally well be used. A slide channel 35 is mounted adjacent a marginal side edge of frame 30, in which a slide 36 is slidably and releasably lockably mounted. Slide 36 is provided with a plate 37 rigidly mounted perpendicular to the direction of movement of said slide and carrying at the outward end thereof a protractor scale 38, calibrated in degrees on each side of a zero mark. Superimposed on plate 37 a second cursor or straight 39 is pivotally mounted on slide 37 by a pivot pin 40 in the same plane as the zero mark on scale 38.

In use the frame 30 is placed horizontally across the patients back with the members 31 depending vertically downwardly. Center mark 32 is aligned with the longitudinal axis of the spine and members 31 are then frictionally slid up and down in contact with the skin across the entire profile of the back under examination. The highest point on one side is noted. In FIG. 3, this is illustrated as the member bearing number 10 right. Slide 36 is then moved up or down as required so that pivotally mounted cursor 39 can pass through both left and right members bearing number 10. Cursor 39 can then be used to read off the hump angle directly on protractor 38 (6.5° in this illustrative example). It will, of course, be appreciated that the positioning of slide 36, scale 38 and cursor 39 relative to the finger member 31 is not important but merely a matter of design convenience and that, indeed any form of straight edge which need not necessarily be pivotally mounted on the slide may be employed to determine the angle $\phi$ subtended between the horizontal and the line between the locators on respective ones of the selected pair of members 31.

We claim:

1. A device for use in the preliminary evaluation of scoliosis, comprising:
   a frame;
   a plurality of stiff, parallel, laterally spaced elongated members arranged in pairs along a side edge of the frame with the two members of one pair being equally spaced on opposite sides of a centerline of the side edge, said elongated members being longitudinally frictionally slidable through the frame parallel to the centerline of the side edge thereof;
   means on said frame for aligning said centerline with a patients' longitudinal spinal axis; and
   means on said frame to determine an angle defined as a rib hump angle and subtended between a first line perpendicular to the movement of the elongated members and a second line intersecting said first line and passing through a selected position on each respective member of a selected said pair of members, and comprising scale means slidably mounted on said frame for movement parallel to said movement of said elongated members including line means corresponding to said first line, and cursor means pivotally mounted on said scale means for alignment with said second line.

2. A device as claimed in claim 1, including levelling means on said frame.

3. A device as claimed in claim 2 wherein said levelling means is a spirit level means mounted on said frame.

4. A device as claimed in claim 1 wherein each said pair of elongated members is provided with pair identifying indicia.

5. A device as claimed in claim 4 wherein said indicia comprises a numerical mark.

6. A device as claimed in claim 1 wherein each said pair of elongated members is provided with pair identifying indicia and each member of a said pair is provided with a locator mark at a selected position thereon.

* * * * *